US008835119B2

(12) United States Patent
Roos et al.

(10) Patent No.: US 8,835,119 B2
(45) Date of Patent: Sep. 16, 2014

(54) LECTIN PATHWAY DEFICIENCY ASSAY

(75) Inventors: Johanna Roos, VV Katwijk ZH (NL); Mohamed R. Daha, CH Leiderdorp (NL); Lee H. Bouwman, PZ Leiden (NL); Cornelis Erik Hack, ND Diemen (NL)

(73) Assignee: Euro Diagnostica AB, Malmo (SE)

( * ) Notice: Subject to any disclaimer, the term of this patent is extended or adjusted under 35 U.S.C. 154(b) by 1929 days.

(21) Appl. No.: 10/521,038

(22) PCT Filed: Jul. 11, 2003

(86) PCT No.: PCT/SE03/01211
§ 371 (c)(1),
(2), (4) Date: Oct. 31, 2005

(87) PCT Pub. No.: WO2004/011674
PCT Pub. Date: Feb. 5, 2004

(65) Prior Publication Data
US 2006/0148015 A1  Jul. 6, 2006

(30) Foreign Application Priority Data

Jul. 26, 2002  (SE) ...................................... 0202325
Sep. 30, 2002  (SE) ...................................... 0202880

(51) Int. Cl.
*A61K 39/395*  (2006.01)
*C07K 16/18*  (2006.01)
*G01N 33/564*  (2006.01)
*G01N 33/68*  (2006.01)

(52) U.S. Cl.
CPC .............. *G01N 33/564* (2013.01); *G01N 33/68* (2013.01)
USPC ...... 435/7.1; 435/334; 424/144.1; 424/130.1; 424/133.1

(58) Field of Classification Search
None
See application file for complete search history.

(56) References Cited

U.S. PATENT DOCUMENTS 6,297,024 B1  10/2001  Hugli et al.

FOREIGN PATENT DOCUMENTS

WO  02/06460 A2  1/2002

OTHER PUBLICATIONS

Fredrikson et al. "New procedure for the detection of complement deficiency by ELISA: Analysis of activation pathways and circumvention of rheumatoid factor influence". *Journal of Immunological Methods* 1993, vol. 166, pp. 263-270.
Gupta-Bansal et al. "Inhibition of complement alternative pathway function with anti-properdin monoclonal antibodies". *Molecular Immunology* 2000, vol. 37, pp. 191-201.
Kuipers et al. "A hemolytic assay for the estimation of functional mannose-binding lectin levels in human serum". *Journal of Immunological Methods* 2002, vol. 268, pp. 149-157.
Petersen et al. "An assay for the mannan-binding lectin pathway of complemnet activation". *Journal of Immunological Methods* 2001, vol. 257, pp. 107-116.
Roos et al. "Specific Inhibition of the Classical Complement Pthway by C1q-Binding Peptides". *The Journal of Immunology* 2001, vol. 167, 7052-7059.
Suankratay et al. "Requirement for the alternative pathway as well as C4 and C2 in complement-dependent hemolysis via the lectin pathway". *The Journal of Immunology* 1998, vol. 160, pp. 3006-3013.
Zimmerman-Nielsen et al. "Complement activation mediated by mannan-binding lectin in plasma from healthy individuals and from patients with SLE, Crohn's disease and Colorectal cancer. Suppressed activation by SLE plasma". *Scand. J. Immunol.* 2002, vol. 55, pp. 105-110.
Horiuchi et al. "II. Progress in diagnosis of connective tissue disease and understanding of its clinical condition, 7. Complement." *Jr. of the Japanese Society of Internal Medicine.* vol. 87. No. 12. 1998. pp. 2427-2433. (No Translation).
Fujita et al. Recent Progress for molecular mechanism of protection against infection-Role complement-lectin pathway in protection against infection. *Clinical Immunity.* vol. 35. No. 1. 2001. pp. 38-43. (No Translation).
Hoekzema et al. "The Distortive Mechanism for the Activation of Complement Component C1 Supported by Studies with a Monoclonal Antibody Against the "Arms" of C1q." *Molecular Immunology.* vol. 25. No. 5. 1988. pp. 485-494.
Collard et al. "Complement Activation after Oxidative Stress: Role of the Lectin Complement Pathway." *Am. Jr. of Pathology.* vol. 156. No. 5. 2000. pp. 1549-1556.
Horiuchi et al. "II. Progress in diagnosis of connective tissue disease and understanding of its clinical condition, 7. Complement." *Jr. of the Japanese Society of Internal Medicine.* vol. 87. No. 12. 1998. pp. 2427-2433. (Abstract Translation).
Fujita et al. Recent Progress for molecular mechanism of protection against infection-Role complement-lectin pathway in protection against infection. *Clinical Immunity.* vol. 35. No. 1. 2001. pp. 38-43. (Abstract Translation).
Roos et al., "Functional characterization of the lectin pathway of complement in human serum.", *Molecular Immunology* 39 (2003) 655-668.
Laich et al., "Complement C4bC2 complex formation: an investigation by surface plasmon resonance," *Biochimica et Biophysica Acta* (2001) 1544: 96-112.

*Primary Examiner* — Lisa J Hobbs
(74) *Attorney, Agent, or Firm* — Merchant & Gould P.C.

(57) ABSTRACT

The invention refers to an in vitro method of functionally determining at physiological conditions deficiencies in the lectin pathway of the complement system, the method comprising the steps of (a) providing a sample of mammalian blood, serum, plasma or another body fluid; (b) preventing in the sample the activation of the classical pathway by contacting the sample with an inhibitor of a molecule of the C1 complex of the complement system; (e) preventing in the sample the activation of the alternative pathway; (d) activating the lectin pathway in the sample; and (e) determining in the sample any activation of the autologous C5b-9 complex. The invention also refers to a kit for functionally determining in a body fluid from a mammal deficiencies in the lectin pathway of the complement system, which kit comprises the separate items (a) an inert carrier and a substance activating the lectin pathway; (b) a diluent comprising an inhibitor of a molecule of the C1 complex; and an antibody against the autologous C5b-9 complex.

8 Claims, 11 Drawing Sheets

A

B

A

B

C

D

A

B

LECTIN PATHWAY DEFICIENCY ASSAY

Figure 1:
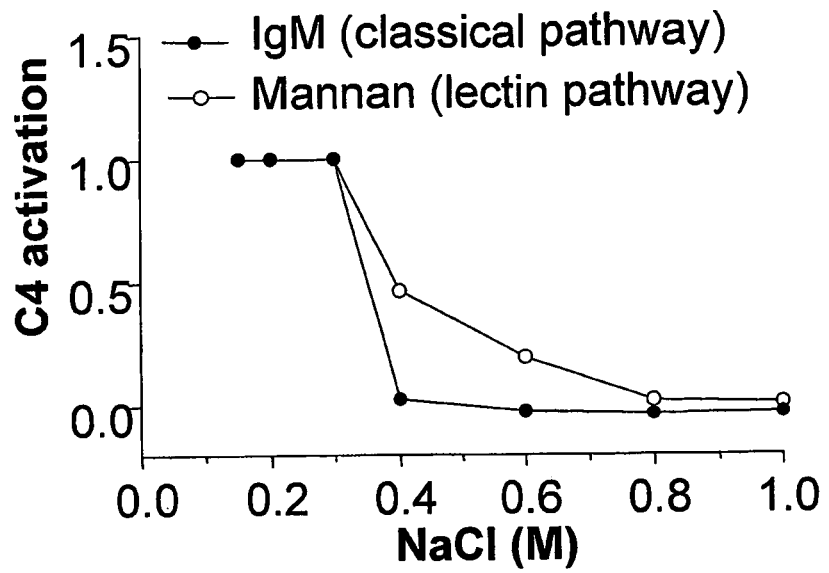
Figure 1:
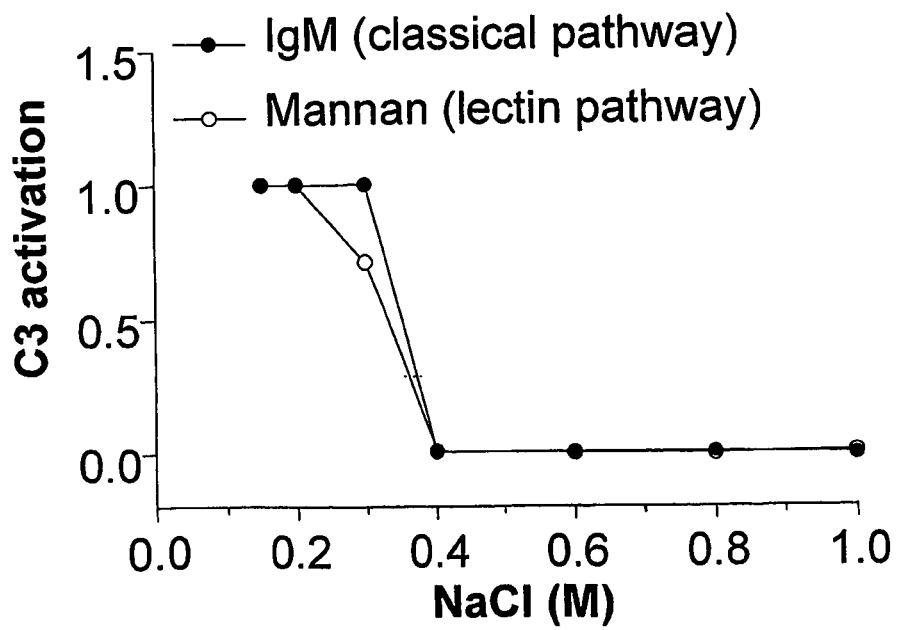

The invention refers to assaying the complement system. More specifically, the invention refers to a method as well as a kit for functionally determining deficiencies in the lectin pathway of the complement system at physiological conditions.

The complement system is a complex part of the innate immune system, which comprises a number of plasma proteins and transmembrane proteins that interact with each other. The term innate immunity is used in order to differentiate this type of immunity from that termed adaptive immunity. However, complement also plays a role in adaptive immunity, but is much less understood in this connection.

A series of soluble proteins present in serum aid, when activated, in the elimination of microorganisms and other antigens from tissues and from the blood. This is achieved either by the complement components alone, or by their subsequent interaction with cells expressing complement receptors which triggers other arms of the immune response.

In order to prevent host tissues from being damaged, the complement system has to be strictly regulated. The large number of proteins, present either in serum or expressed on cell surfaces are involved as complement regulatory molecules in the protection of host cells, in the control of complement during activation by antigen, and in the de-activation of complement once antigen has been eliminated.

As a major component of host defence against pathogenic organisms, the activation of the complement system is of key importance for the innate defense against invading pathogens. In higher organisms, animals respond to the antigenic challenge presented by invading organisms by the development of a specific immune response. Antibody is formed and cells that have the capacity to recognize the specific foreign antigen are generated. Thus, the complement identifies its target via direct recognition of the microbial surface by complement components, as well as via indirect binding to adaptor molecules such as antibodies or acute phase proteins. Subsequent activation of the complement system generally results into elimination of the activator via humoral and cellular mechanisms. These defense functions of the complement system are required for optimal host immunity.

For example, the mannan-binding lectin (MBL) is able to bind to repetitive saccharides frequently present on the surface of many clinically relevant microorganisms. This direct binding of MBL is involved in the elimination of pathogens by the immune system. The importance of MBL in innate resistance against invading pathogens is clearly illustrated by persons with genetic mutations in the MBL gene. These mutations lead to structural abnormalities of the MBL molecule, resulting in impaired complement activation via the lectin pathway, which is associated with an increased susceptibility to infections.

The activation of the complement system is an important component of host defense. Following infection, triggering of the complement activation cascade via direct binding of complement components to a microbial surface may lead to opsonisation and pathogen elimination via humoral and cellular mechanisms. Furthermore, complement activation may trigger and amplify the acquired immune system.

In addition to playing an important role in host defense against infection, the complement system is a mediator in both the pathogenesis and prevention of immune complex diseases. It has a protective effect when functioning in moderation against appropriate pathogens, since an inflammation promoted by complement activation at the same time can result in cellular damage when not properly controlled.

The cascade reaction of complement activation can be triggered via at least three known activation pathways, i.e., the classical pathway (CP), the alternative pathway (AP), and the lectin pathway (LP). These three pathways converge at the component C3. The terminal complement pathway consists of all proteins activated after C3, and results into assembly of the C5-9 group of proteins into the membrane attack complex (MAC). The MAC exerts powerful killing activity by creating perforations in cellular membranes.

Defects in the complement system may lead to a partial or complete blockade of the complement activation cascade. Depending on the level of the defect, either the induction phase or the effector phase of complement activation may be hampered, and the defect may affect more than one pathway. An impaired function of the complement system may occur due to genetic defects, or due to acquired deficiencies of complement components. Acquired complement deficiencies may occur due to formation of autoantibodies to complement components or due to excessive complement consumption. Genetic complement deficiencies have been described at all levels of the system.

Most complement defects are associated with disease, ranging from a relatively mild increase in the susceptibility to infections to the occurrence of a severe systemic autoimmune syndrome. Furthermore, an impaired complement function is associated with the occurrence of flares in patients with systemic lupus erythematosus (SLE). Therefore, functional assays to measure complement activity in human serum have a clear diagnostic and prognostic value.

However, during the last years it has become increasingly clear that complement components via similar mechanisms may target its effects to damaged self tissue. Thereby, the complement contributes to the amplification of tissue damage and inflammation in conditions such as autoimmune diseases, immune complex diseases, Alzheimer's disease, and ischemia/reperfusion injury as occurring in e.g. myocardial infarction, stroke, and major surgery. For example, recent studies have also provided evidence that activation of the lectin pathway by MBL can be responsible for complement activation and related inflammation in ischemia/reperfusion injury as well as myocardial infarction. Furthermore, complement activation contributes to the pathogenesis of allograft and xenograft rejection. Thus, undesired activation of complement is involved in inflammation and associated tissue damage in a number of pathological conditions.

It is difficult to pinpoint and functionally determine deficiencies in the complement system. Defects may lead to a block in the complement cascade at the point of the defect. In general, patients with defects in the classic pathway proceed down the pathway until the point of defect, and the latter proteins in the cascade are not recruited. On the other hand, individuals with abnormalities of the alternative pathway are less common than are individuals with abnormalities of the classical pathway and, in some cases, only a few individuals with the abnormality have been described.

Functional deficiencies in the lectin pathway are usually due to genetic polymorphisms in the MBL gene. Among the complement deficiencies described in humans, deficiency of MBL has the highest frequency. These deficiencies have a clear clinical significance, both by increasing the susceptibility to infections and by enhancing the progression of chronic diseases.

Deficiencies in the complement cascade can lead to overwhelming infection and sepsis. Deficiencies in complement mainly predispose patients to infection via two mechanisms, i.e. ineffective opsonization and defects in lytic activity (defects in MAC).

An example is the presence of defects that result in inadequate opsonization. Opsonization is the process of coating a pathogenic organism so that it is more easily ingested by the macrophage system. The complement protein C3b, along with its cleavage product C3bi, is a potent agent of opsonization in the complement cascade. Any defect that causes decreased production of C3b results in inadequate opsonization ability. Such opsonization defects can be caused by deficiencies in components of the classical, alternative, or MBL pathways, or defects may be caused by deficiencies of the C3 component itself.

The complement function is mostly measured by using hemolytic assays, which enable the functional assessment of the classical complement pathway and the alternative complement pathway, respectively. In these hemolytic assays, the function of the complement pathways is expressed as its ability to generate the C5b-9 complex upon activation. Such an assay is currently not available for the lectin pathway of complement. In view of the high frequency of MBL deficiency in the human population, a reliable assay to measure lectin pathway function is highly warranted.

Usually, a method for detecting complement or its deficiency in the blood is performed by means of tedious haemolytic and antigenic methods. Increased or decreased levels of different components of complement pathways are assayed. Such tests require targeting antibodies, which will recognize specific complement proteins. Generally, antigenic assays of complement proteins in serum or plasma are the most readily available tests, particularly for C3. In the latter assays, the serum level of C3 is provided, but it tells little or nothing about the functional activity. Hypofunctional variants exist, but no non-functioning C3 variants are described.

When studying functional complement, sheep erythrocytes have been used, since they are easily lysed by antibody and complement. The most commonly performed test for functional complement activity is the $CH_{50}$, a measure of the ability of a dilution of the serum of a patient in order to lyse an antibody coated sheep erythrocyte. When for example one of the proteins of the classic pathway is missing, lysis in the $CH_{50}$ assay is blocked, the functional titer of the deficient protein being close to zero, and the $CH_{50}$ obtained is zero. An alternative pathway lytic test exists and is termed the $AP_{50}$. This test is less sensitive than the $CH_{50}$ test and is used as a screening test.

In order to detect functional deficiencies of the letin pathway, it is important to design a functional assay in such a way that for example antibody-mediated activation of the classical pathway does not interfere in the detection, leading to false positive results. This is important since anti-carbohydrate antibodies directed against MBL-ligands that are used as activators of the lectin pathway are common in the human population, and since these antibodies can result into complement activation via the classical pathway in MBL-deficient serum. Therefore, a reliable functional lectin pathway assay should prevent activation of the classical complement pathway.

The assays available until now for determining deficiencies in the lectin pathway have serious restrictions, and can not determine the functional activity of the whole activation cascade. Either they use exogenous complement (and measure only the activity of the MBL-MASP complex) or they use endogenous C4 (but not later activation steps) by using an assay under artificial conditions that largely inhibits physiological complement activation.

In an article by Zimmermann-Nielsen et al. (Scand. J. Immunol. 55:105-110, 2002) an assay for quantitating MBL-induced activation of the complement system in human plasma is disclosed. In this assay complement activation was determined as autologous C4 activation. The initiation of the alternative pathway was blocked by using a high ionic strength diluent buffer (1 M NaCl) as serum incubation buffer.

However, the presence of 1 M NaCl strongly hampers activation of C4 both for the classical pathway and for the lectin pathway. Therefore, this assay does not really discriminate between these two pathways but makes both of them highly inefficient. Furthermore, this leads to the necessity of using extremely high serum concentrations (1/5) in this assay, since these suboptimal conditions result in a strongly inhibited complement activation which is close to the detection limit.

Thus, complement activation in this Zimmerman-Nielsen assay is not measured under physiologic conditions, and the artificial conditions provided are likely to have differential effects on sera from different sources and/or different MBL genotypes. In addition, it is not possible in this assay to assess complement activation at a later stage than C4, since the formation of C4b2a is strongly dependent on ionic strength (Laich and Sim, BBA 1544:96-112, 2001), and a C3 activation is accordingly completely undetectable in 1 M NaCl, also at high serum concentrations.

Thus, there is a need of methods for the functional identification at physiological conditions of deficiencies in the lectin pathway of the complement system of a mammal, including humans. Such a method should allow for a specific assessment of the complete lectin pathway of complement activation until formation of C5b-9.

The purpose of the invention is to achieve a method of functionally determining in vitro deficiencies in the complement system whereby the above-mentioned problems are eliminated.

In order to achieve this purpose an in vitro method of functionally determining at physiological conditions deficiencies in the lectin pathway of the complement system is provided, the method comprising the steps of
    (a) providing a sample of mammalian blood, serum, plasma, or another body fluid;
    (b) preventing in the sample the activation of the classical pathway by contacting the sample with an inhibitor of a molecule of the C1 complex of the complement system;
    (c) preventing in the sample the activation of the alternative pathway;
    (d) activating the lectin pathway in the sample; and
    (e) determining in the sample any activation of the autologous C5b-9 complex.

The purpose of the invention is also to produce a kit for functionally determining deficiencies in the lectin pathway of the complement system in a sample from a body fluid.

This purpose is achieved by means of a kit which comprises the separate items
    (a) an inert carrier and a substance activating the lectin pathway;
    (b) a diluent comprising an inhibitor of a molecule of the C1 complex; and
    (c) an antibody against the autologous C5b-9 complex.

According to the invention an in vitro method of functionally determining at physiological conditions deficiencies in the lectin pathway (LP) of the complement system via autologous complement is provided. In the inventive method a sample of mammalian blood, serum, plasma, or another body fluid is first provided by means of methods well-known within the art. The activation of two non-assayed pathways, i.e. the classical pathway (CP) and the alternative pathway (AP), is then prevented in the sample, and the lectin pathway is activated. At last, any activation of the complement pathway is determined at the level of the C5b-9 complex.

The inventive procedure has to take a multitude of facts and problems into consideration. For example, the large multimeric protein complex C1 of the complement system is composed of the subunits C1q, C1r, and C1s. The activation of the classical pathway starts with the binding of a foreign antigen by specific antibodies to form immune complexes, e.g. IgM. Each immunoglobulin Fc region has a single C1q-binding site, and each C1q must bind to 2 heavy chains to be activated (thus either 2 IgG which become cross-linked or 1 IgM).

In the classical complement pathway the recognition unit C1q is strongly related to the family of proteins known as collectins, which have a complex structure made up of trimers consisting of, a segment of a collagenous sequence at its N-terminus, and a C-type lectin domain at its C-terminus. C1q does not possess a lectin domain, but shares many structural and functional features with the collectins. The plasma concentration of C1q amounts to around 100 μg/ml, and in vitro experiments show that only a small fraction of C1q is sufficient for a complete complement activation.

In the inventive method potent and specific complement inhibitors are used to prevent undesired activation of each complement pathway. At least two different types of inhibitors of C1q can be used to prevent the activation of the classical pathway, those binding to the globular heads and interfering with ligand recognition, and those binding to the collagenous tail and impairing the interaction with complement activating enzymes and/or C1q receptors. Obviously, those inhibitors which interfere with ligand binding inhibit an earlier step of classical pathway activation. On the other hand, molecules that bind to the globular head of C1q may trigger a C1 activation in the fluid phase, especially when these C1q-binding molecules are multimeric.

Preferably, monoclonal antibodies directed against C1q are used in order to efficiently inhibit C1q-mediated ligand binding and complement activation.

A number of identified molecules are shown below in Table 1, which can regulate the functional activity of C1q.

TABLE 1

| Inhibitor | Description/comments | Mechanism of C1 inhibition |
|---|---|---|
| C1 inhibitor | Plasma serine protease inhibitor | Inhibits C1r and C1s activity |
| IVIg | Has broad activity | Blocks C1q ligand binding |
| CRT | Contains several active domains | May inhibit both C1q head and C1q tail |
| C1Qr | Native C1q receptor | Binds C1q tail, inhibits C1 formation |
| E. coli C1q binding protein | | Binds C1q tail, inhibits C1 formation |
| gC1qR | Native C1q receptor | Binds C1q head |
| Decorin | Matrix protein | Binds to C1q head and tail preparations |
| Chondroitin sulphate proteoglycan | plasma proteoglycan/B cell-secreted | Inhibits C1 formation |
| Surfactant protein A | Collectin present in the lung | Inhibits C1q ligand binding and C1 formation |
| HNP-1 | Cytotoxic peptide produced by neutrophils | Binds C1q tail and inhibits C1 formation |
| Peptide gC1q-$R_{18}$ (TDGDKAFVDFLSDEIKEE: SEQ ID NO 1) | Derived from gC1qR | Not defined |
| Peptide KDIRCKDD (SEQ ID NO. 2) | Derived from CRT | Inhibits C1q ligand binding |
| Peptide AEAKAKA (SEQ ID NO. 3) | Derived from human IgG | Inhibits C1q ligand binding |
| Peptide VQVHNAKTKPR (SEQ ID NO. 4) | Derived from human IgG1 | Not defined |
| Peptide WY | Derived from human IgG | Inhibits C1q ligand binding |

TABLE 1-continued

| Inhibitor | Description/ comments | Mechanism of C1 inhibition |
| --- | --- | --- |
| Peptide 2J (CEGPFGPRHDLTFCW SEQ ID NO. 5) | Synthetic peptide | Binds C1q head, inhibits ligand binding |
| ghB3 | Trimeric C1q B chain | Acts as a competitor for C1q binding |
| Peptide CBP2 LEQGENVFLQATLL (SEQ ID NO. 6) | Derived from C1q B chain | Acts as a competitor for C1q binding |

In Table 1, natural C1q-binding molecules, several series of C1q-binding peptides and competitive inhibitors derived from the sequence of C1q are shown, which can be used in the method according to the invention for inhibiting C1q of the complement system or as a inhibitory C1q-binding protein when preventing the activation of the classical pathway.

The classical C1q-binding proteins are immunoglobulins, and the globular head domain of C1q interacts with both IgG and IgM upon antigen binding, or after its aggregation or immobilization. Human immunoglobulin for intravenous use (IVIg) can inhibit complement activation, and the main mechanism of action seems to be a scavenging of C1q and activated C4 and C3 by soluble immunoglobulins.

Next to immunoglobulins, a number of other proteins have been identified that are able to bind C1q. Among these are C1q-binding proteins, which (under certain conditions and on certain cell types) are present on the cell membrane, such as calreticulin (CRT), the endothelial C1q receptor, and the globular C1q receptor (gC1q-R). The membrane-expressed forms of these C1q binding proteins are involved in C1q-mediated cell activation, whereas soluble forms of these molecules are able to inhibit C1q function.

Calreticulin (CRT) is a calcium-binding protein that is mainly present in the lumen of the endoplasmic reticulum. Protein sequencing data indicate that CRT probably is identical to the C1q receptor present on the cell surface of various cell types. CRT can bind to the α2 macroglobulin receptor (CD91) at the cell surface, and different domains of CRT can be distinguished, which bind to C1q, i.e. the adjacent N domain and P domain, but not the C domain. Furthermore, the S-domain, which overlaps parts of the N- and P-domains, also shows clear C1q binding. The S-domain of CRT clearly resembles a CUB domain present in C1r and C1s, suggesting that this domain may interact with the collagenous part of C1q.

Accordingly, different sites on C1q interact with different domains of CRT. Native and recombinant CRT, as well as the N-domain, the P-domain and the S-domain, all inhibit the C1q-dependent hemolysis as well as the formation of C1. A number of C1q-binding peptides have also been identified that are able to inhibit C1q function, which peptides are useful in the present inventive method. Among these are human neutrophil peptide-1, peptides derived from natural C1q-binding proteins, and synthetic peptides selected from peptide libraries.

A C1q-binding protein (gC1qR) can also be used, which binds specifically to the globular head of C1q. The native C1q receptor (C1qR), isolated from human endothelial cell membranes or from polymorphonuclear leukocyte membranes, functionally inhibits the formation of active C1. This inhibitory activity is reversed by C1q collagenous tails, but not by globular heads. In a similar way, a soluble protein isolated from *E. coli*, which binds C1q, is able to inhibit C1 formation.

In addition, the activation of the classical pathway can be prevented by contacting the sample in an assay with an antibody directed against C1r or C1s. In this connection several other C1q-binding molecules can be used, which can modulate C1q function. Examples are the C1q-associated plasma proteoglycan and the chondroitin sulfate proteoglycan produced by human B cells, which can bind C1q and inhibit C1 formation. The dermatan sulfate proteoglycan decorin, a constituent of the extracellular matrix, as well as the related proteoglycan biglycan are also suitable inhibitors.

Likewise, the activation of the classical pathway can be prevented by providing a peptide inhibitor of C1r or C1s. Several members of the pentraxin family, i.e. C reactive protein, serum amyloid P component and pentraxin-3, have been described to bind C1q. Pentraxin-3 can inhibit C1q activity under certain conditions, and surfactant protein A, a member of the collectin family, is able to bind to C1q and to inhibit its activity. This is accomplished by interfering in both the binding of C1r and C1s as well as the binding of immune complexes.

A competitive inhibition of C1q by C1q-derived molecules is an alternative approach for the inhibition of the classical complement pathway. Here, functionally inactive parts of the C1q molecule are used, which each serves as a competitive inhibitor for C1q ligand binding. Recombinant globular head domains of the C1q A (ghA) and B chain (ghB) have been generated, which separate domains are both able to bind to IgG, but the B domain is more potent than the A domain. A better activity is obtained when the recombinant C1q B chain is trimerized by using the neck region of the surfactant protein D.

A small inhibitory C1q-binding molecule can also be used, such as the human neutrophil peptide-1 (HNP-1), which can bind to C1q and inhibit the classical complement pathway. This peptide belongs to the α defensin family of small cationic peptides, which are present in azurophilic neutrophil granules. It is preferred that such a peptide inhibitor of C1r or C1s is a synthetically produced peptide in order to achieve sufficient amounts at low costs.

Several C1q-binding peptides have been identified on basis of the amino acid sequence of C1q binding proteins. By using 92 overlapping peptides, several C1q binding sites in the N and P regions of CRT have been identified. A number of these peptides are able to inhibit a classical pathway activation in human serum as well as the binding of C1q to IgG. These peptides are characterized by a motif that resembles a binding site for C1q in the CH2 domain of IgG (ExKxKx).

In this connection, peptides directly derived from IgG have been described to inhibit C1q, such as a 7-meric peptide (i.e. AEAKAKA SEQ ID NO. 3) containing the ExKxKx motif, an 11-meric peptide (VQVHNAKTKPR SEQ ID NO. 4) derived from IgG1 that is related to the same motif, and a dimeric peptide (WY, c.f Table 1). These peptides were able to inhibit activation of the classical complement pathway in several in vitro assays. However, the WY peptide also inhibits the alternative complement pathway.

Among 42 peptides selected from phage-displayed peptide libraries based on phage binding to human C1q, 20 peptides have been identified, which can inhibit the classical complement pathway in human serum. Remarkably, 13 out of these 20 peptides were able to inhibit the classical pathway as well as the alternative pathway in hemolytic assays, whereas 7 peptides specifically inhibited the classical pathway. Out of these peptides, the peptide 2J (CEGPFGPRHDLTFCW SEQ ID NO. 5) was selected. Peptide 2J is a strong inhibitor of C1q hemolytic function. Similar to the peptides with an IgG motif, peptide 2J binds to the globular head of C1q and inhibits the binding of C1q to IgG. In addition, peptide 2J inhibits C1q from human, primate and rodent origin.

Other selected peptides useful for inhibiting the classical pathway are CEGPFGPRHDLTFCW (SEQ ID NO. 5), CRWDGSWGEVRC (SEQ ID NO. 7), CMWVRMWGDVNC (SEQ ID NO. 8), CFWAGKFGLGTC (SEO ID NO. 9), CKDRWVVEERCC (SEQ ID NO. 10), and CWNRFKKMDRC (SEO ID NO. 11). Several other peptides can also be used, which act as a competitor for C1q binding and are derived from the C1q B chain, e.g. the peptide CBP2 (LEQGENVFLQATLL SEQ ID NO. 6).

The C1 inhibitor protein is a key molecule with respect to complement regulation at the recognition phase and inhibits the serine proteases of the activated C1 complex. Thus, any potentiator of the C1 inhibitor can be used in order to prevent the activation of the classical pathway.

In addition, a protease inhibitor of C1r or C1s can be used, for example known inhibitors of serine proteases. These inhibitors can also be used when the activation of the lectin pathway is to be prevented.

The mannan-binding lectin (MBL) is a C-type lectin present in serum in a large pro-enzymatic complex that shows similarities with C1. Similar to C1q, MBL is a polymeric molecule of trimeric subunits. The trimers of MBL consist of three identical chains with a collagenous tail region and a carbohydrate recognition domain. In serum, MBL is associated with the MBL-associated serine proteases MASP-1, MASP-2, and MASP-3. It has been demonstrated that activated MASP-2 is able to activate C4 and C2, which results in the formation of the C3 convertase C4b2a and the subsequent activation of C3. The MASP enzymes are homologous to C1r and C1s.

A simple and effective way to prevent the activation of the alternative pathway is to dilute the sample. By addition of 1 M NaCl to a serum dilution buffer, C1q binding and CP activation can be completely prevented whereas binding of MBL can proceed. However, the inhibiting effects of high ionic strengths should be taken into consideration.

In the alternative pathway, the serine protease factor D produces a C3 convertase which—if not inactivated—will continue to act on component C3 and cause its total depletion. Thus, the activation of the alternative pathway can prevented by contacting the sample in an assay with a protease inhibitor of factor D of the complement system or an antibody directed against the same.

The lectin pathway is known to be activated by the binding of the members of collectin family of proteins to specific carbohydrate moieties on invading pathogens. These then directly activate the components of the classical pathway, the need for specific antibodies being avoided. One member of the collectin family is mannan-binding lectin (MBL), which is found in serum and binds to terminal mannose groups on bacteria.

Accordingly, the lectin pathway can be activated by contacting the sample with a MBL-binding carbohydrate of high or low molecular weight. Examples of high molecular weight mannans are glucomannans and galactomannans. Preferably, the MBL-binding carbohydrate of low molecular weight is mannose or fucose. The lectin pathway can also be triggered by binding of a synthetic carbohydrate conjugate or a microbial polysaccharide.

Since ficolins, GlcNAc-binding lectins in serum, are considered to be lectins with the ability of activating the lectin pathway, the lectin pathway can also be activated by providing in an assay a ficolin-binding carbohydrate.

However, certain pathogens have the ability to directly activate the classical pathway, without the need for specific antibody interactions. Activating molecules include yeast cell walls, bacterial lipopolysaccharide (LPS) and the capsids of several viruses. Likewise, aggregates of immunoglobulins, for example, IgA or IgE are known to activate the alternative complement pathway. Thus, when preventing the activation of one pathway, an activator should not be used in the inventive method, which itself activates this pathway.

Any activation of the complement pathway in the sample can subsequently be determined by establishing an activation of a complement protein from C4 to C9 of the same. Preferably, SC5b-9, the terminal complement complex, is determined since it is the membrane attack complex (MAC, C5b-9) that is formed when complement activation occurs by either pathway. The determination can be accomplished by providing in an assay antibodies against the autologous C5b-9 complex formed.

It should be noted that in the inventive method the antibody against the C5b-9 complex recognizes the whole complex and not its individual parts.

In a complement function assay a certain density of an activating substance is required. For example, an antibody must be bound, e.g. to an antigen or to a plastic material, in order to activate complement. Likewise, any activation of the complement should be performed by determining the binding of any complement protein from C4 to C9; or of any formed C5b-9 complex, to an activating surface.

Thus, it is preferred in the kit according to the invention that the activating substance is coated (immobilised) on an inert carrier. A coating on the surface of a carrier can be accomplished by using conventional techiques. For example, the activating substance can be immobilized by means of covalent coupling to the carrier as a bead or matrice/gel.

Suitable carriers for attachment of the substance activating the lectin pathway are synthetic polymeric carriers, such as polypropylene, polystyrene, substituted polystyrene, e.g. aminated or carboxylated polystyrene, polyacrylamides, polyamides, polyvinylchloride etc, glass, agarose, nitrocellulose etc. The carrier can be in the form of beads, strips, or wells of microtitre plates. Preferably, an ELISA plate is used. However, other carriers can also be used.

Separate items to be included in a kit for carrying out inventive method are:
(a) an inert carrier and a substance activating the lectin pathway;
(b) a diluent comprising an inhibitor of a molecule of the C1 complex;
(d) an antibody against the C5b-9 complex.
(e) a labeled anti-antibody against the antibody against the C5b-9 complex;
(f) an enzyme substrate;

(g) a washing solution;
(h) a normal body liquid; and
(i) an inactivated normal body liquid.

Preferably, the kit is used in an ELISA analysis when carrying out inventive method. Such a kit can be used manually or in a robot. A software system for flexible automated multi-well plates analyses can also be utilized.

When a deficiency in the lectin pathway of the complement system is suspected, a body fluid obtained from a patient, usually a serum, can be analyzed by means of the inventive method. The serum, a negative, and a positive control are all diluted in the same way with a diluent.

The diluent comprises an inhibitor of a molecule of the C1 complex in order to inhibit the classical pathway and is preferably the C1q inhibitor. Other inhibitors mentioned above can also be used.

The diluent can be formulated from buffered aqueous media containing a variety of salts and buffers. Preferably, the salts are alkali and alkaline earth halides, e.g. sodium chloride, potassium chloride, or sodium sulphate. Various, such as buffers may be used, such as citrate, phosphate, HEPES, Tris or the like to the extent that such buffers are physiologically acceptable for its purpose. The diluent should have a physiological pH and a physiological ionic strength. Preferably, phosphate buffered saline (PBS) is used. The diluent should contain calcium and magnesium ions.

The negative control is an inactivated normal body liquid. In this case, the inactivated normal body liquid is heat inactivated human serum. The negative control defines the lowest possible signal which can be obtained with the inventive method, not only the lectin pathway but the total complement system being completely extinguished.

The positive control is a serum sample from a person with a normal level of complement. Such a control is included in the kit in order to estimate if a signal is plausible or not when determining in the sample any activation of the C5b-9 complex.

The positive control can also be a serial dilution (calibrator) of a normal serum for a calibration curve, which is used for a quantification of the method. Such a calibration can be used for selecting a standard value, by means of which it is possible to compare different patients or follow the treatment of a patient.

After dilution of the serum to be tested as well as the positive and negative controls, the liquids are allowed to contact the inert carrier and the substance activating the lectin pathway.

In a not limiting exemplifying embodiment of the invention the carrier is in the form of a strip coated with mannan. Each strip with diluted serum, positive and negative control sera are incubated at 37 C. for 30 min, thereby activating the complement, and the terminal complex is formed.

The strips are then washed with the washing solution, which in this embodiment should be the buffer component of the diluent.

A diluent buffer solution of a labeled mouse anti-antibody against the antibody against the C5b-9 complex is then added to the strips, which are incubated for further 30 min. The anti-antibody can be enzyme labeled or labeled in some other way, e.g. fluorescent labeled. Preferably, the label is an enzyme. It is also preferred that the antibody is a monoclonal antibody, most preferred a monoclonal anti-mouse antibody.

The antibody against the C5b-9 complex can also be directly labeled for generating a signal, such as a fluorescent or enzyme label, preferably labeled with an enzyme, the anti-antibody step being omitted.

The strips are again washed and an enzyme substrate in a suitable reaction buffer is then added. The reaction between enzyme labeled anti-mouse antibody and enzyme substrate is allowed to proceed for 30 min, and the color of reaction product is measured in as spectrophotometer, a deficiency in the test serum corresponding to a low absorbance with reference to the positive control serum.

EXAMPLES

The method of the present invention will now be further illustrated by but is by no means limited to the following examples.

Materials and Methods
Human Materials.

Human serum was obtained from 70 healthy adult volunteers and immediately frozen at −80° C. in aliquots. Outdated healthy donor plasma was obtained from the Bloodbank Leiden-Haaglanden, Leiden, the Netherlands. From a patient with Kahler's disease of the IgM type, plasma was obtained that became available after a plasmapheresis treatment.

Anti-C1q and anti-MBL antibodies.

Monoclonal antibodies against C1q were produced in mice as described before (Hoekzema R., et al. *Mol. Immunol.* 25, 485-494, 1988). The anti-C1q mAb 2204 (IgG1) is directed against the globular head domain of C1q and is able to inhibit the binding of C1q to IgG, as well as C1q-dependent hemolysis (Roos A., et al., *J. Immunol.* 167, 7052-7059, 2001). For the purification of mAb 2204, gamma globulins were precipitated from ascites by using 50% $(NH_4)_2SO_4$. The precipitate was dialyzed against 10 mM Tris containing 2 mM EDTA (pH 7.8) and subjected to anion exchange chromatography by using DEAE-Sephacel (Pharmacia, Uppsala, Sweden). Proteins were eluted by using a salt gradient and the fractions that showed binding of mouse IgG to C1q-coated ELISA plates in the presence of 1 M NaCl were pooled, concentrated, dialyzed against PBS and stored at −80° C.

Polyclonal anti-C1q antibodies were produced in rabbits. New Zealand White rabbits were immunized (weekly for four weeks) with 180 μg C1q dissolved in complete Freunds adjuvant, resulting in antisera with a positive titer on C1q-coated ELISA plates beyond 1/25,000. IgG was precipitated from rabbit serum by using 40% $(NH_4)_2SO_4$ and purified by using DEAE-Sephacel as described above.

Starting from purified rabbit IgG anti-C1q, Fab fragments were generated by using papain. Therefore, IgG was dialyzed against 10 mM phosphate buffer containing 10 mM L-cysteine and 2 mM EDTA (pH 7.0). Subsequently, mercuripapaine (from Sigma) was added (1% w/w of the protein content) followed by incubation for 16 hours at 37° C. After dialysis against PBS, the sample was applied to Sepharose-coupled protein G (from Pharmacia, Uppsala, Sweden), and the fall through fractions, containing Fab fragments, were pooled, concentrated, and used for experiments. Analysis by non-reducing SDS-PAGE showed a prominent band at approximately 45 kD.

A mouse mAb directed against the lectin domain of human MBL (mAb 3F8) was kindly provided by Dr. G. L. Stahl (Harvard Medical School, Boston, Mass., USA) (Collard C. D., et al., *Am. J. Pathol.* 156, 1549-1556, 2000).

Preparation of Human C1q and C1q-Depleted Serum.

Human C1q was isolated from human donor plasma exactly as described previously and was stored at −80° C. (Roos A., et al., *J. Immunol.* 167, 7052-7059, 2001). Isolated C1q was able to completely restore the lysis of antibody-coated erythrocytes induced by C1q-depleted human serum.

For the preparation of C1q-depleted serum, undiluted normal human EDTA plasma (obtained from a donor with the MBL/AA genotype) was applied on column consisting of Biogel A5 (from Biorad) coupled to rabbit IgG anti-human C1q. The column was washed by using Veronal-buffered saline (VBS; 1.8 mM Na-5,5-diethylbarbital, 0.2 mM 5,5-diethylbarbituric acid, 145 mM NaCl) containing 10 mM EDTA. Fractions were tested in a C1q-dependent hemolytic assay in the absence or presence of purified C1q. Fractions that showed complete erythrocyte lysis in the presence of C1q, but not in the absence of C1q, were pooled and concentrated until the original volume. After recalcification, C1q-depleted serum was stored at −80° C.

Isolation of Human IgM.

Plasma containing an IgM paraprotein was dialyzed against 10 mM sodium acetate containing 2 mM EDTA (pH 5.0). The precipitated proteins were recovered by centrifugation, dissolved in PBS, dialyzed against Tris/EDTA buffer (10 mM Tris, 2 mM EDTA, pH 7.8 and conductivity 5.0 mS), and subjected to anion exchange chromatography by using DEAE-Sephacel. The IgM eluted by the salt gradient was pooled, dialyzed against 10 mM sodium acetate (6.0 mS, pH 7.0) and applied to a CM-C-50 Sephadex anion exchange column (from Pharmacia). Following elution with a salt gradient, fractions containing IgM were pooled, concentrated, and applied to a Superdex 300 gel filtration column. Peak fractions containing IgM and free of IgG were pooled, concentrated, and stored at −80° C.

In the drawings

FIG. 1 shows the activation of C4 (A) and C3 (B) as assessed by ELISA of human serum incubated on plates coated with mannan in a buffer containing calcium, magnesium, and NaCl.

Figure 2:
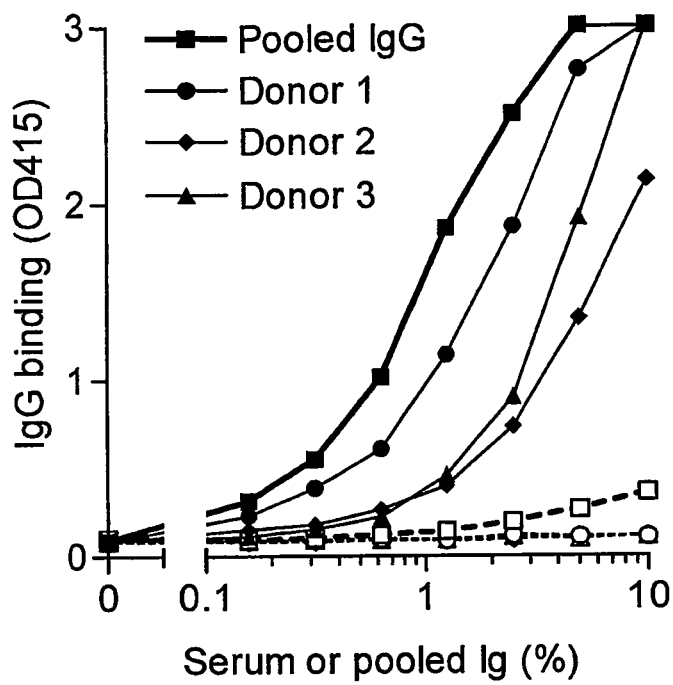
Figure 2:
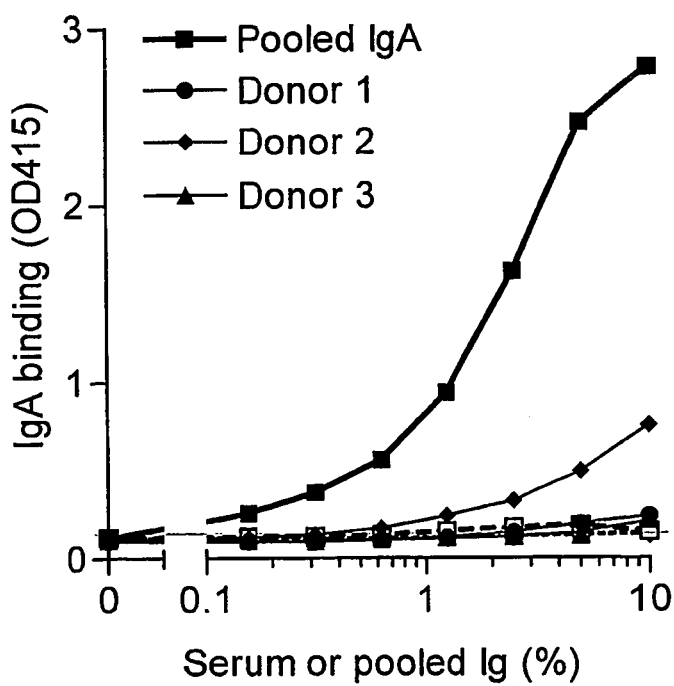
Figure 2:
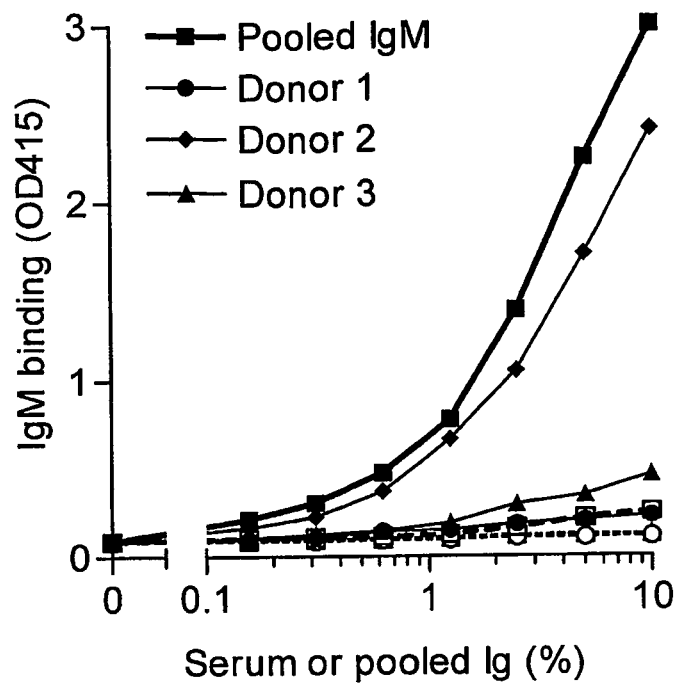
Figure 2:
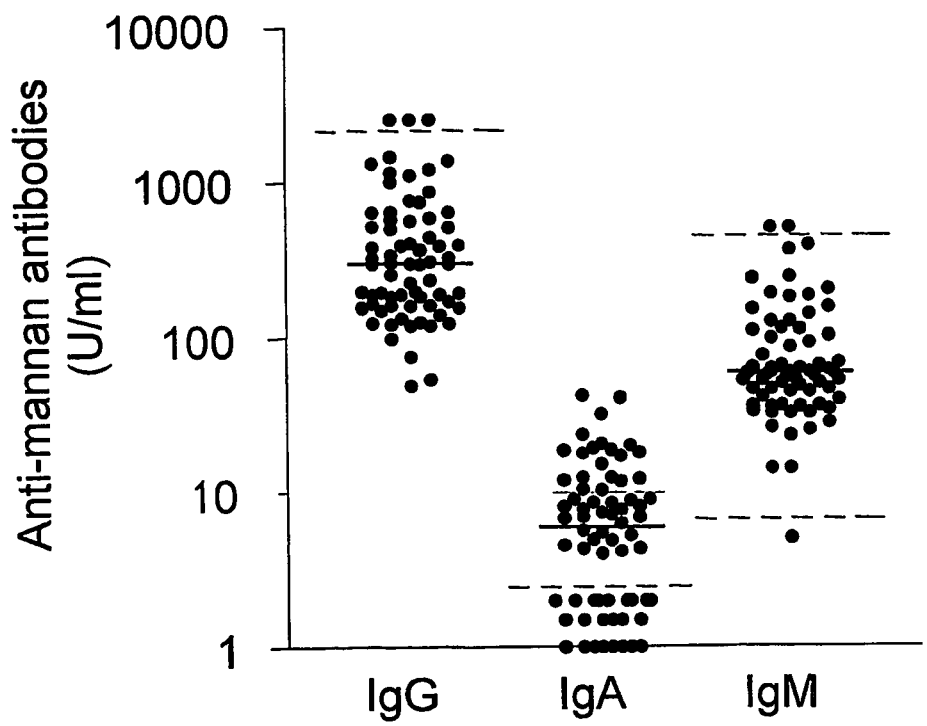

FIG. 2 shows anti-mannan-antibodies in human serum;
A-C: Different concentrations of human serum from three different healthy donors were incubated on plates coated with either mannan (closed symbols, solid lines) or BSA (open symbols, dashed lines). Binding of IgG (A), IgA (B) or IgM (C) was detected. As a positive control, plates were incubated with pooled immunoglobulin, as indicated;
D: Anti-mannan antibodies of the three major Ig classes were quantified in healthy donor serum (N=70). Solid lines indicate the median concentrations, dashed lines indicate the detection limits.

Figure 3:
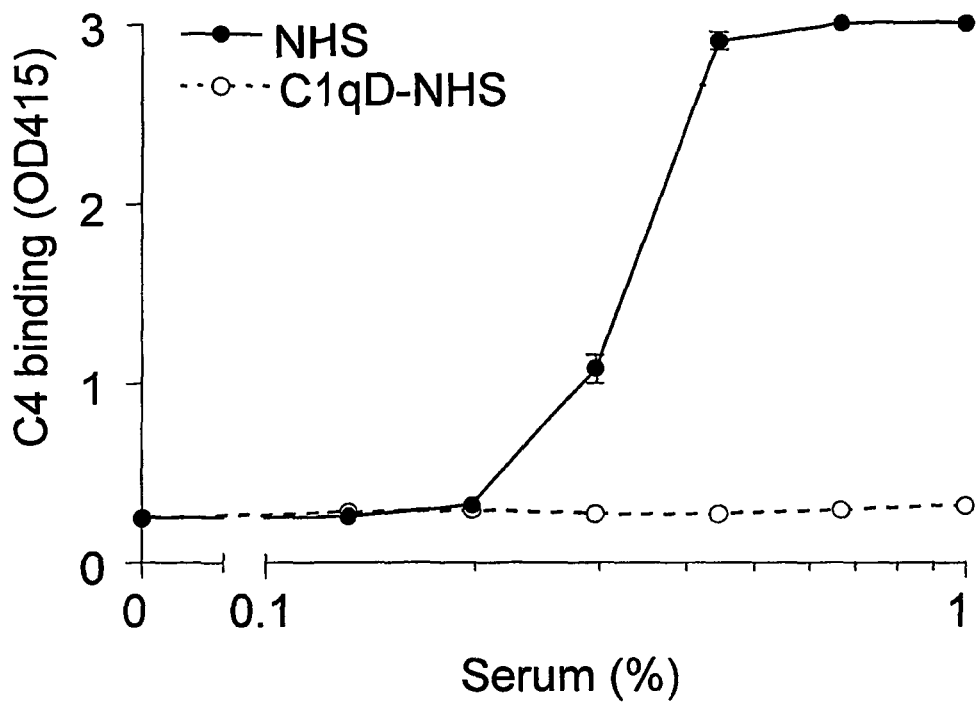
Figure 3:
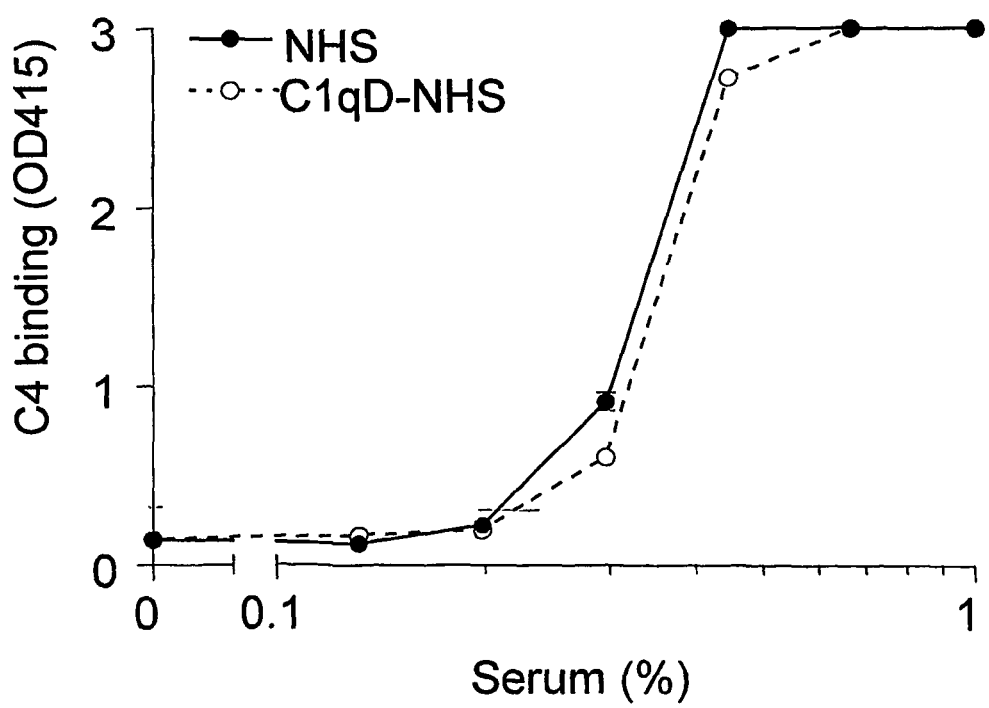
Figure 3:
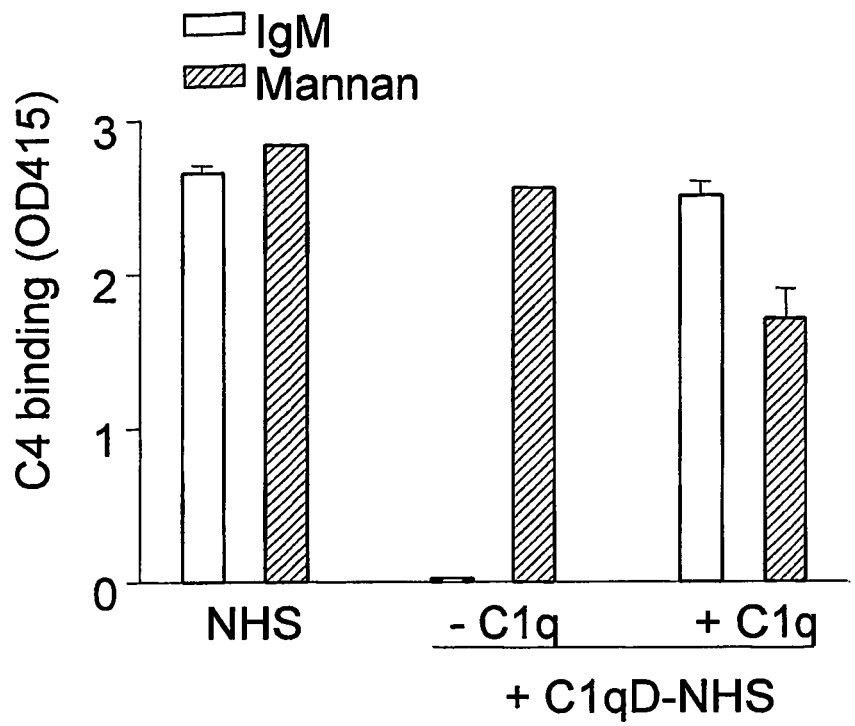
Figure 3:
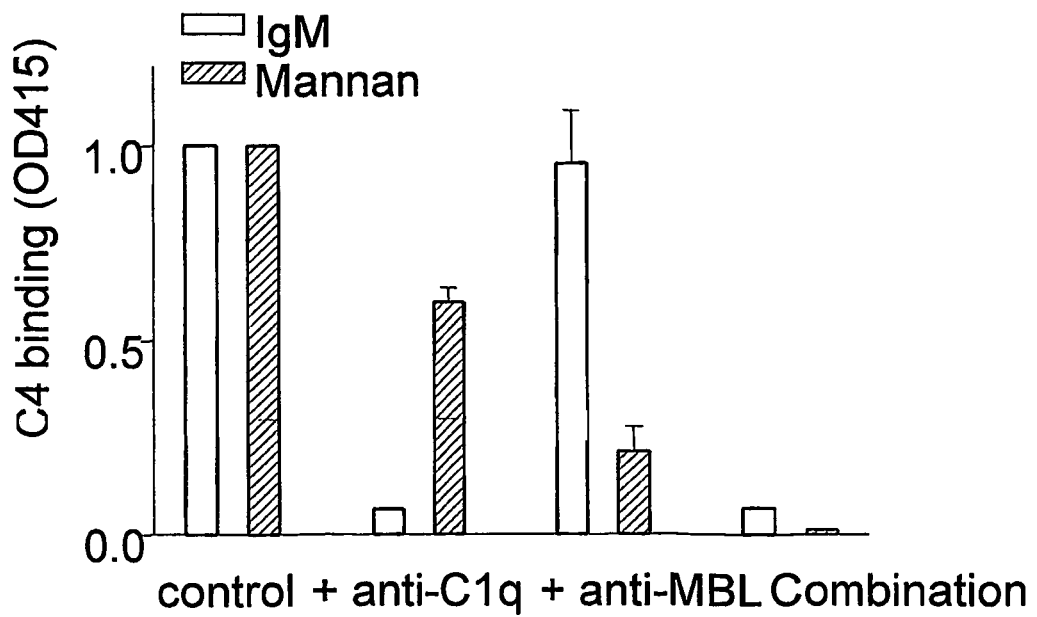

FIG. 3 shows the role of C1q in activation of the CP and the LP;
A, B: Normal human serum or C1q-depleted serum (C1qD-NHS), diluted in GVB++, was incubated on plates coated with IgM (A) and mannan (B), respectively, followed by detection of C4 binding;
C: NHS and C1q-depleted NHS (diluted 1/400) were incubated on plates coated with IgM or mannan in the presence or absence of purified C1q (0.5 µg/ml), as indicated.
D: NHS was incubated on IgM- or mannan-coated plates in the presence or absence of blocking mAb directed against MBL (mAb 3F8, 10 µg/ml) or C1q (mAb 2204, 20 µg/ml), or both (combination).

FIG. 4A-B shows the assessment of C4 activation with purified IgG (A) and IgM antibodies (B), respectively, in concentrations as indicated, which were incubated on mannan coated plates with MBL-deficient serum in the absence or presence of mAb 2204 anti-C1q.

FIG. 5A-H shows complement activation via the LP and the CP; Complement activation was induced by incubation of different concentrations of NHS on plates coated with IgM for CP activation (A-D) or with mannan for LP activation (E-H), in the presence or absence of mAb 2004 (20 µg/ml). Activation and binding of complement was demonstrated by detection of C1q (A and E), C4 (B and F), C3 (C and G), and C5b-9 (D and H) using specific mAb.

FIG. 6A-B shows activation of the alternative pathway; NHS was incubated on plates coated with mannan, LPS, or BSA, in a calcium-free buffer (GVB/MgEGTA) to block activation of the CP and the LP. Binding of C3 (A) and C4 (B), respectively, was subsequently assessed.

Comparative Example

High salt concentrations influence the complement system negatively, several reactions being inferior.

Serum was incubated in wells of microtitre plates coated with mannan in buffer containing calcium, magnesium, and NaCl at the concentrations indicated in FIG. 1, and the activation of C4 (A) and C3 (B) was assessed by ELISA.

A complete inhibition of the activation of C4 (A) as well as a complete inhibition of the activation of C3 (B) ionic strengths inhibit C3, probaly by means of denaturation, thereby preventing any mesurement of activities after C4.

Example 1

Assessment of Functional Lectin Pathway Activity by ELISA

Functional activity of the lectin pathway was assessed with ELISA by using immobilized mannan as a ligand. Mannan was obtained from Sigma from *Saccharomyces cerevisiae*; M7504), dissolved in PBS (10 mg/ml) and stored at −20° C. Nunc Maxisorb plates (Nunc, Roskilde, Denmark) were coated with mannan (100 µg/ml) in coating buffer (100 mM $Na_2CO_3/NaHCO_3$, pH 9.6) for 16 hours at room temperature or for 2 hours at 37° C. After each step, the plates were washed three times with PBS containing 0.05% Tween 20. Residual binding sites were blocked by incubation for one hour at 37° C. with PBS containing 1% BSA. Serum samples were diluted in GVB++ (VBS containing 0.5 mM $MgCl_2$, 2 mM $CaCl_2$, 0.05% Tween-20, and 0.1% gelatin; pH 7.5) in the presence of mAb 2204 (20 µg/ml) as an inhibitor of C1q, unless otherwise indicated. This mixture was pre-incubated for 15 minutes on ice, before addition to the plates. The plates were then sequentially incubated for 1 hour at 4° C. and for 1 hour at 37° C., followed by washing. Complement binding was detected by using mouse mAb conjugated to digoxygenin (dig) by using digoxygenin-3-O-methylcarbonyl-ε-aminocaproic acid-N-hydroxysuccinimide ester (from Boehringer Mannheim, Mannheim, Germany) according to instructions provided by the manufacturer. Detection of C1q, C4, C3, and C5b-9 was performed by using mAb 2214 (anti-human C1q), mAb C4-4a (anti-human C4d), RFK22 (anti-human C3), and AE11 (anti-C5b-9), kindly provided by Dr. T. E. Mollnes, Oslo, Norway), respectively. Binding of mAb was detected by using dig-conjugated sheep anti-mouse antibodies (Fab fragments) followed by HRP-conjugated sheep anti-dig antibodies (Fab fragments, both from Boehringer Mannheim). All detection antibodies were diluted in PBS containing 1% BSA and 0.05% Tween 20. Enzyme activity of HRP was detected following incubation at room temperature for 30-60 min with 2,2′-azino-bis(3-ethylbenzthiazoline-6-sulfonic acid) (from Sigma; 2.5 mg/ml in 0.1 M citrate/$Na_2HPO_4$ buffer, pH 4.2) in the presence of 0.01% $H_2O_2$. The OD at 415 nm was measured by using a microplate biokinetics reader (EL312e, from Biotek Instruments, Winooski, Vt., USA).

Quantification of Anti-Mannan Antibodies in Human Serum.

For the quantification of anti-mannan antibodies in human serum, ELISA plates were coated with mannan and blocked with 1% BSA in PBS. Serum samples were diluted 1/100 for detection of IgG anti-mannan Ab, 1/10 for detection of IgA anti-mannan Ab, and 1/40 for detection of IgM anti-mannan Ab, respectively, unless otherwise indicated. For quantification, pooled human IgG (48 mg/ml IgG), pooled human IgA (41 mg/ml IgA), and pooled human IgM (35 mg/ml IgM) were used as a standard for detection of IgG, IgA and IgM anti-mannan antibodies, respectively (kindly provided by Biotest Pharma GmbH, Dreieich, Germany). The concentration of anti-mannan antibodies in these preparations was arbitrarily set at 1000 U/ml. All samples were diluted in PBS containing 0.05% Tween 20 and 1% BSA. Antibody binding was detected by using biotinylated HB43 (mouse mAb anti-human IgG), biotinylated HB57 (mouse mAb anti-human IgM) and dig-conjugated 4E8 (mouse mAb anti-human IgA), respectively, followed by either HRP-conjugated streptavidin or HRP-conjugated sheep anti-dig antibodies (both from Boehringer).

Activate the LP of complement. However, human serum contains anti-carbohydrate antibodies, probably resulting from previous microbial contacts. Such anti-carbohydrate antibodies may bind to mannan and the resulting immune complex may contribute to complement activation by mannan via activation of the classical complement pathway (Petersen S. V., et al., *J. Immunol. Methods* 257, 107-116, 2001). Mannan-binding antibodies are clearly detectable in human serum as assessed by ELISA (FIG. 2). Incubation of pooled human IgG (FIG. 2A), IgA (FIG. 2B) and IgM (FIG. 2C) on immobilized mannan resulted in a dose-dependent binding of IgG, IgA, and IgM, respectively, as detected by isotype-specific mAb. As a control, parallel incubations were performed on immobilized BSA, resulting in low or undetectable background binding of pooled Ig. Incubation of three sera from healthy donors on mannan-coated plates resulted in a strong dose-dependent IgG binding in all three sera. In donor 1, IgA and IgM anti-mannan Ab were undetectable, serum from donor 2 contained IgG, IgA, and IgM anti-mannan antibodies, whereas in donor 3 some IgM binding was observed but no IgA binding (FIG. 2A-C). Binding of Ig was undetectable following incubation of serum on BSA-coated plates (FIG. 2A-C). A quantification of anti-mannan antibodies in sera from 70 healthy donors is presented in FIG. 2D. IgG and IgM anti-mannan Ab were present in nearly all donors, with a large interindividual variation, whereas IgA anti-mannan Ab were detected in 63% of the donors. No significant correlation was observed between the three major isotypes of anti-mannan antibodies, or between anti-mannan antibodies and MBL concentrations (not shown).

Example 2

Functional Characterization of the Lectin Pathway in the Presence of C1q-Inhibitory Ab Both the LP and the CP are calcium-dependent and lead to activation of C4. A distinction between both pathways can be made by selection of a specific ligand that induces specific activation of either the LP or the CP. In view of the presence of anti-mannan Ab in human serum, mannan is likely to activate both the LP, via MBL, and the CP, via anti-mannan Ab. Therefore, a strategy was developed to inhibit activation of the CP in order to allow solely the activation of the LP by immobilized mannan, by using inhibitory anti-C1q antibodies.

Anti-C1q antibodies were tested for their ability to inhibit the CP of complement by using immobilized IgM as a specific activator of the CP. Incubation of 1% normal human serum (NHS) on immobilized IgM induces deposition of C4, which could be dose-dependently inhibited by the anti-C1q mAb 2204, by rabbit IgG anti-C1q antibodies and by Fab fragments prepared from this rabbit anti-C1q antibody preparation. Complete inhibition was reached when the antibodies were applied at 5 µg/ml. In contrast, rabbit IgG prepared from non-immunized rabbits did not have an effect on C4 activation via the CP. These antibodies were tested for their effect on complement activation induced by immobilized mannan. Incubation of NHS on mannan induced a dose-dependent deposition of C4 with a maximal activation at a serum concentration of 1%. Addition of a fixed concentration of mAb 2204, Fab anti-C1q fragments, or normal rabbit IgG as a control had a slight inhibitory effect on C4 activation. In contrast, rabbit IgG anti-C1q Ab induced complete inhibition of C4 activation by mannan, most likely due to complement consumption via C1q-anti-C1q complexes. These data show that C1q-inhibitory antibodies can block CP activation completely whereas mannan-induced activation of the LP can proceed in a C1q-independent way.

To further examine the role of C1q in complement activation by mannan and by IgM, NHS was depleted from C1q. Depletion of C1q from NHS resulted in a complete inhibition of C4 activation by immobilized IgM (FIG. 3A), as previously described (Petersen S. V., et al., *J. Immunol. Methods* 257, 107-116, 2001), whereas C4 activation by immobilized mannan was slightly inhibited by depletion of C1q (FIG. 3B). Reconstitution of C1q-depleted serum with purified C1q resulted in a complete restoration of C4 activation by IgM (FIG. 3C). In contrast, C4 activation by mannan was slightly inhibited by the addition of purified C1q to C1q-depleted serum, possibly due to the presence of an inhibitory protein co-isolated with C1q. The contribution of C1q and MBL to C4 activation by IgM and mannan was further studied by using blocking mAb against C1q and MBL, respectively (FIG. 3D). C4 activation on IgM-coated plates was completely inhibited by mAb anti-C1q and no inhibition occurred with a blocking anti-MBL mAb. In contrast, the C4 activation induced by mannan was partially inhibited by mAb anti-C1q and strongly inhibited by mAb anti-MBL. A complete inhibition of mannan-induced C4 activation was achieved when a combination of mAb anti-C1q and mAb anti-MBL was used. Together, these data indicate that IgM-mediated activation of C4 is completely dependent on C1q and does not involve MBL. In contrast, mannan-induced activation of C4 is mainly mediated by the LP but comprises a minor contribution of the CP. The latter contribution of the CP can be inhibited by C1q-blocking Ab, thus allowing activation of the LP only.

Example 3

Demonstration of Cooperation between the Classical Pathway and the Lectin Pathway in Complement Activation by Mannan The complement-activating capability of anti-mannan antibodies was further assessed in functional experiments by using purified IgG and IgM from normal human plasma. The antibodies were incubated on mannan-coated plates using PBS containing 1% BSA, 0.05% Tween 20, and 10 mM EDTA as a dilution buffer. Following washing, plates were incubated with MBL-deficient serum (diluted 1/100 in the presence or absence of mAb 2204), and activation of C4 was assessed as described above.

Figure 4:
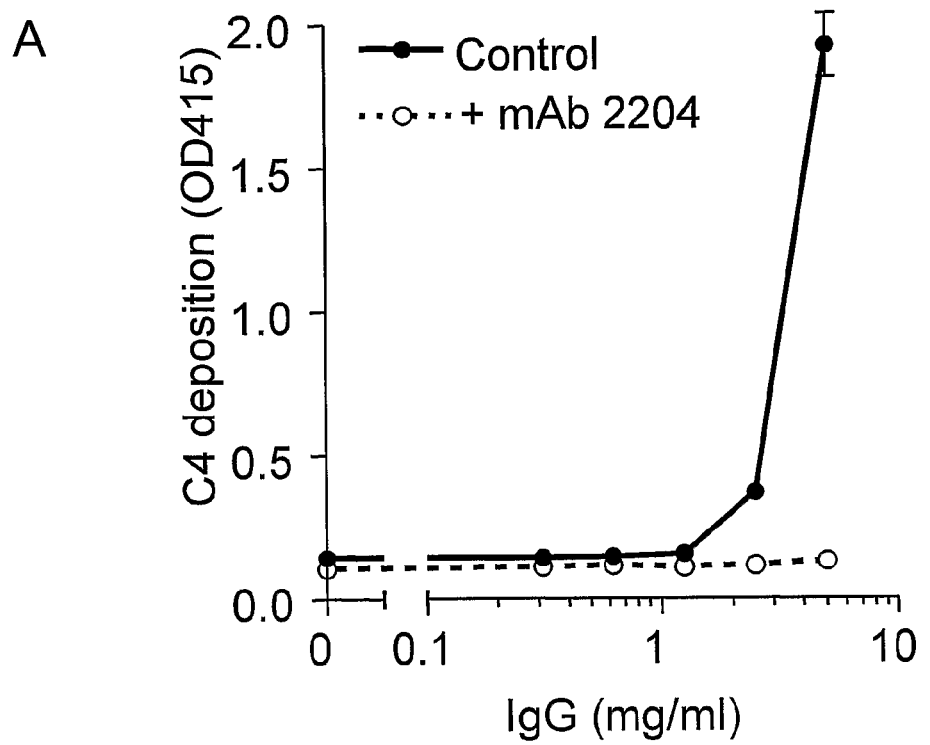
Figure 4:
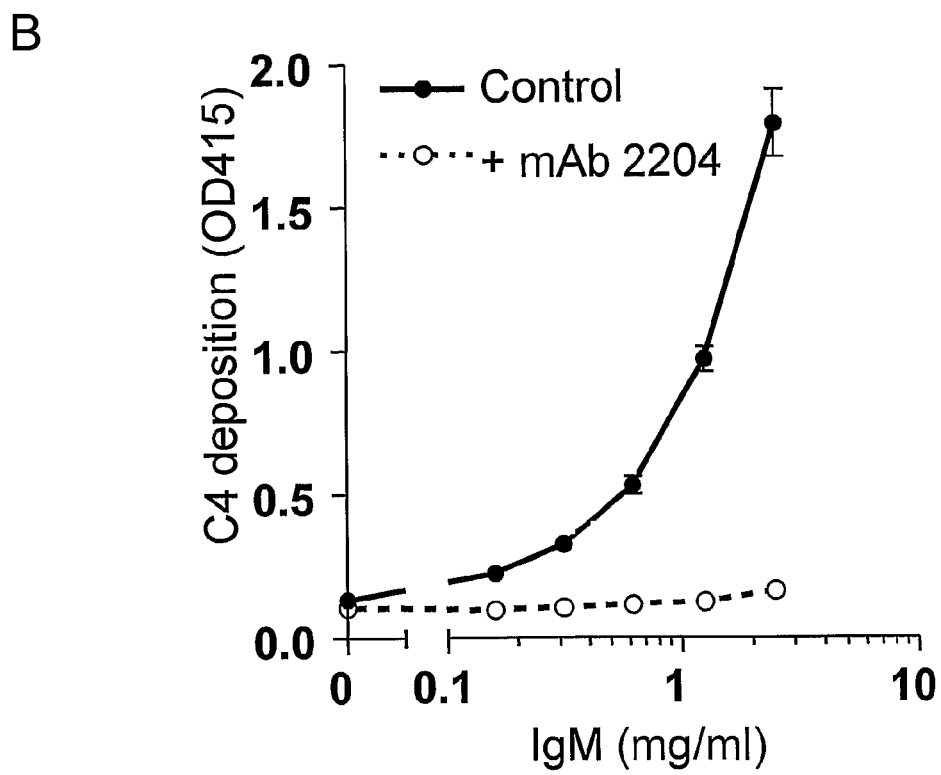
Figure 5:
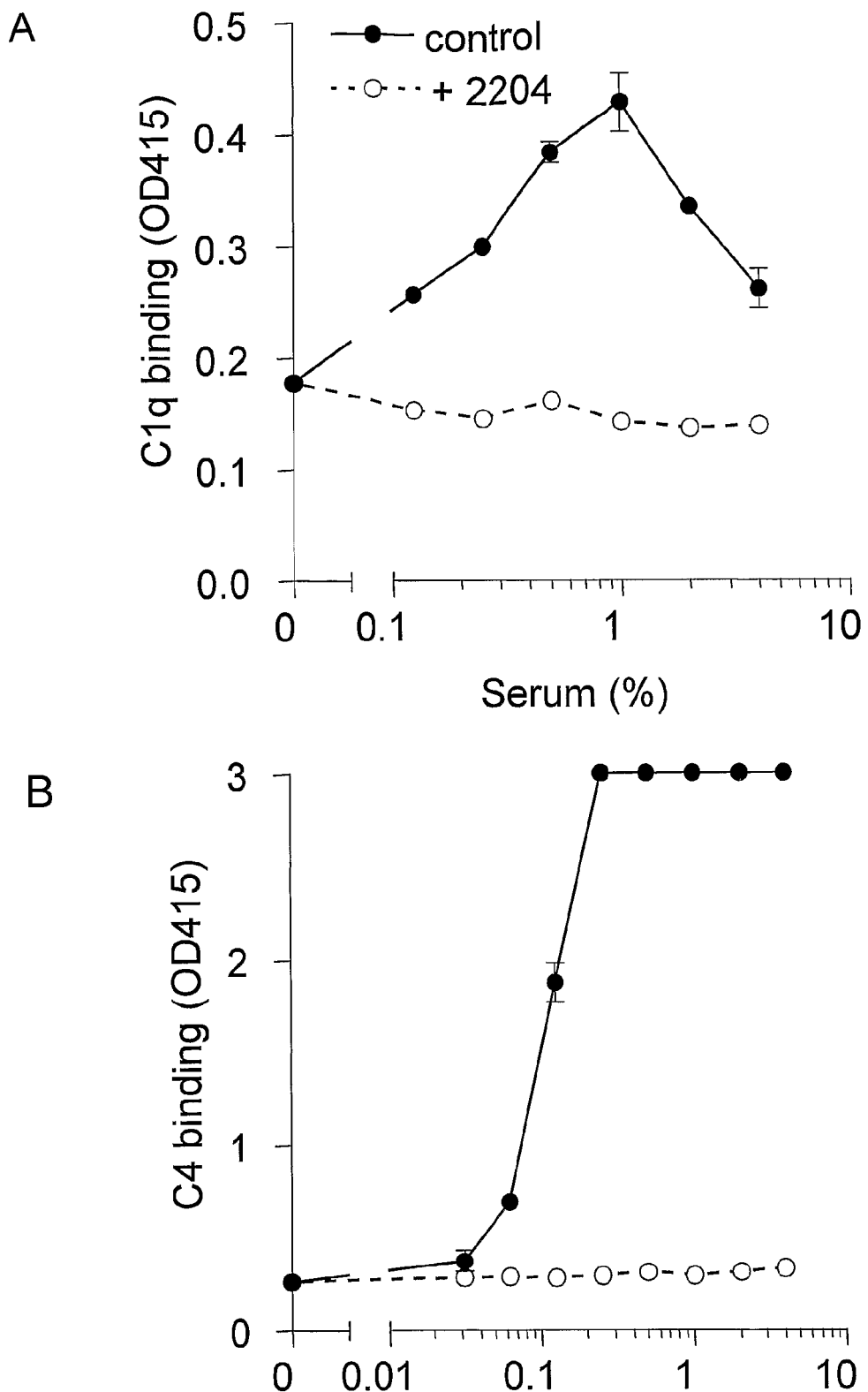
Figure 5:
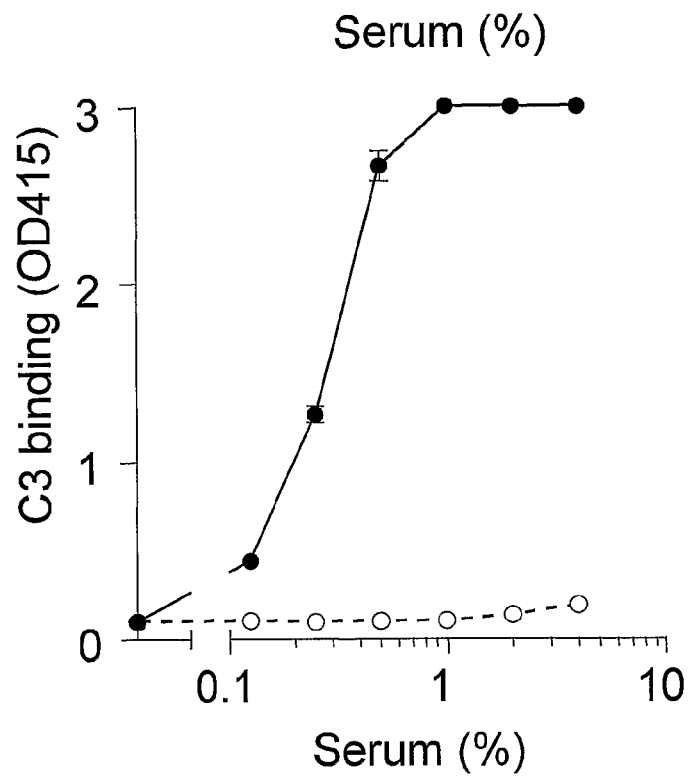
Figure 5:
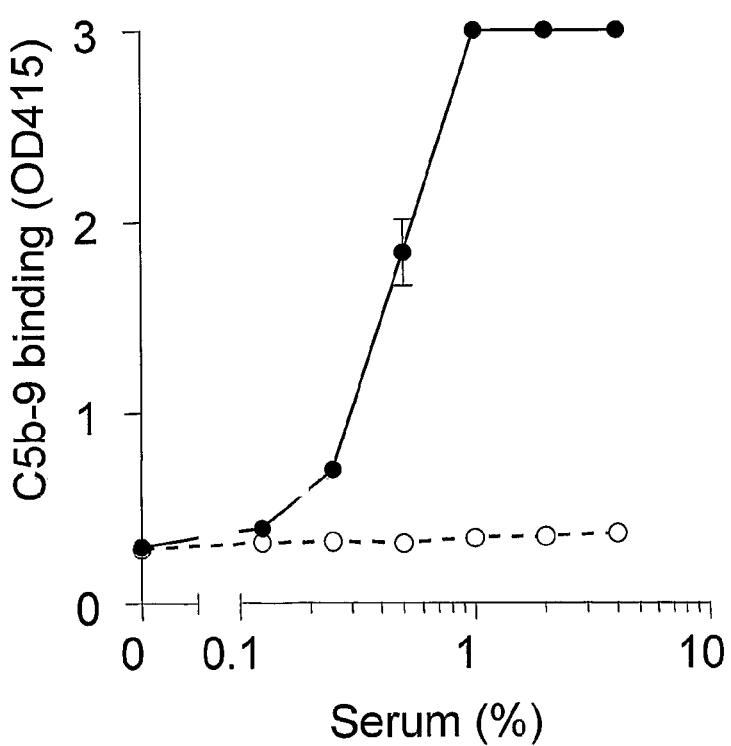
Figure 5:
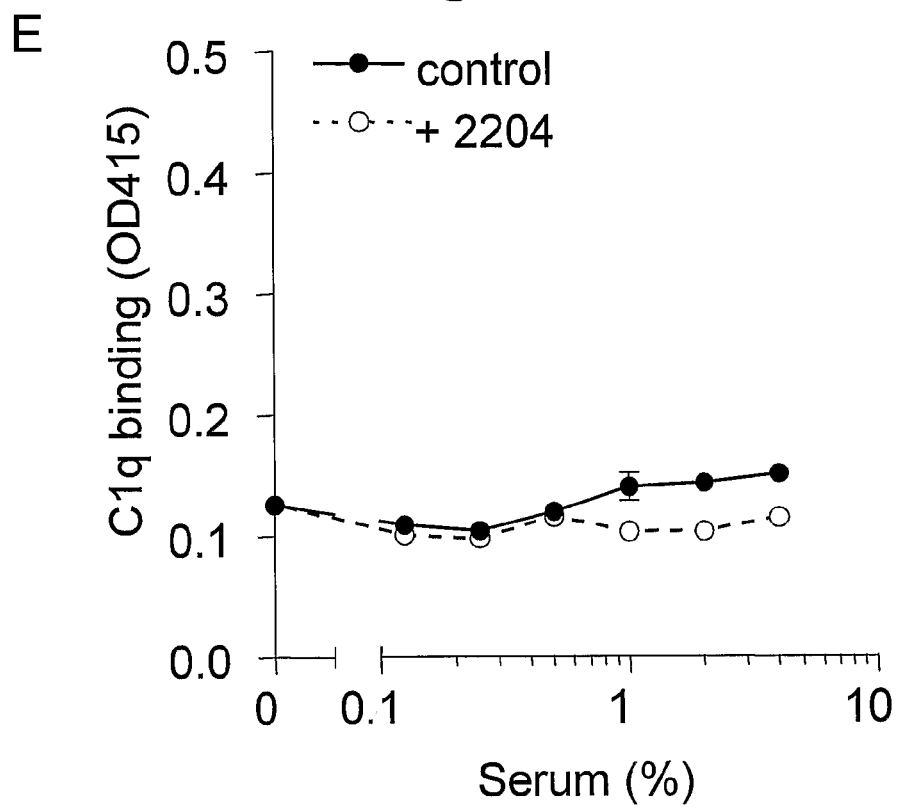
Figure 5:
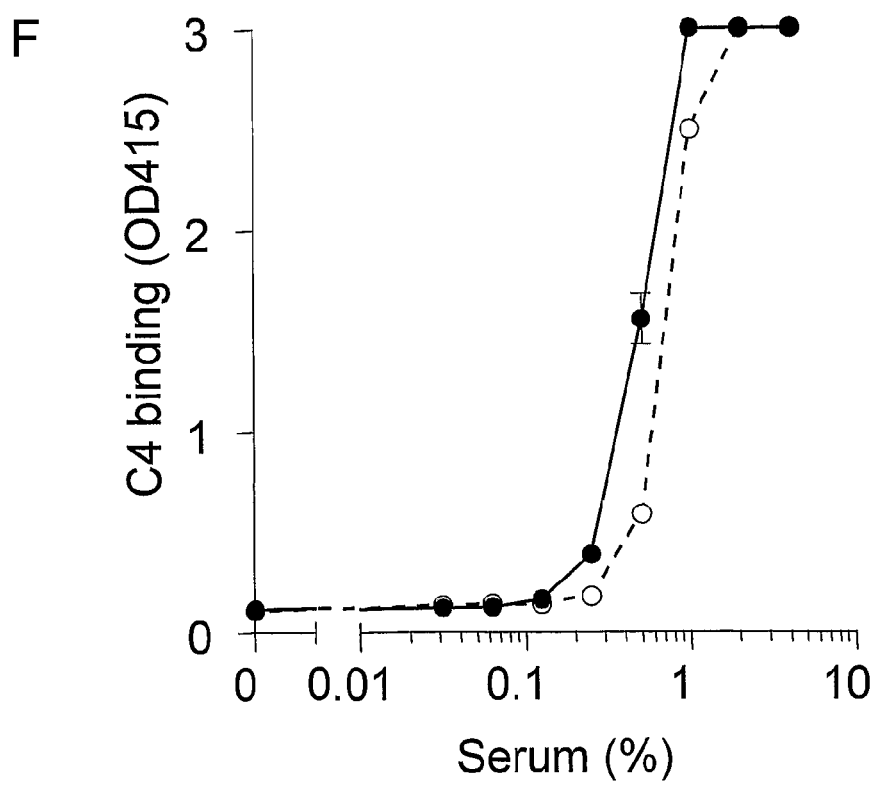
Figure 5:
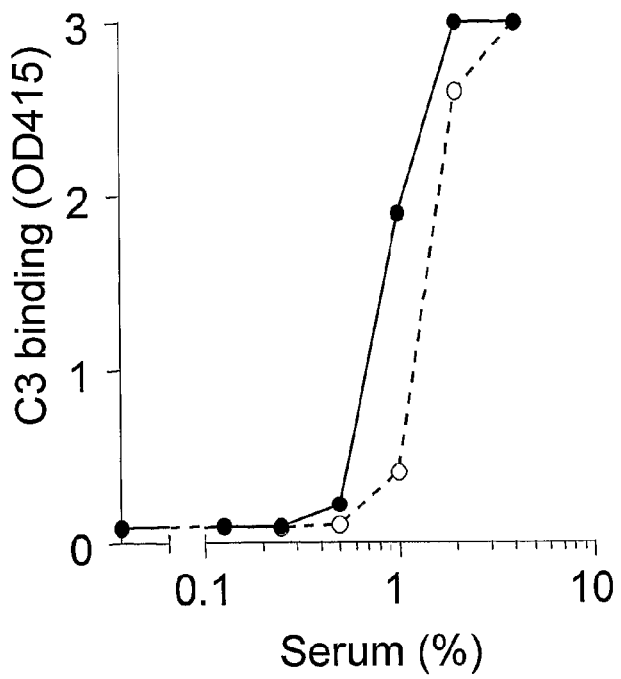
Figure 5:
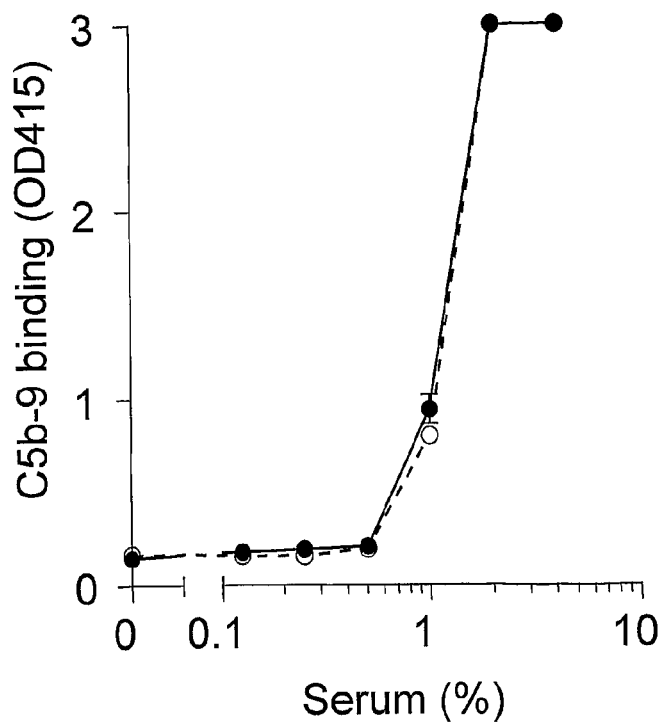

The C4 depletion, as measured by OD415 in ELISA, in the absence or presence of mAb 2204 anti-C1q is shown in FIG. 4. Pre-incubation of mannan-coated plates with purified IgG (Fig 4A) or IgM (FIG. 4B) induced a dose-dependent deposition of C4 on mannan upon addition of MBL-deficient serum (BB genotype), whereas no complement activation could be detected with this serum alone. Activation of C4 induced by anti-mannan Ab was completely inhibited by addition of a C1q-inhibitory Ab in the MBL-deficient serum, clearly indicating that mannan-binding IgG and IgM can restore complement activation by mannan in MBL-deficient serum by the activation of the classical pathway of complement, in the absence of functional MBL.

Example 4

Assessment of Functional Classical Pathway Activity by ELISA

The protocol for the functional activity of the classical pathway was similar to the protocol for the LP assay, Example 1, with important modifications. As a ligand for CP activation, human IgM was coated at 2 µg/ml. After blocking of residual binding sites, serum samples, diluted in GVB++, were added to the plate and incubated for 1 hour at 37° C. Complement binding was assessed by using dig-conjugated mAb directed against C1q, C4, C3, and C5b-9, followed by the detection of mAb binding by using HRP-conjugated sheep anti-dig antibodies.

Example 5

Complement Activation and Formation of C5b-9 via the CP and via the LP

The complement activation cascade was further studied by using mAb to detect binding of specific complement components upon their activation via the CP and the LP, respectively. Incubation of NHS on immobilized IgM resulted in a dose-dependent deposition of C1q, C4, C3, and C5b-9 to the plate (FIG. 5A) (FIGS. 5A-D). Binding the C1q and a subsequent complement activation induced by IgM could be completely inhibited by mAb 2204. Incubation of NHS on immobilized mannan resulted in a dose-dependent binding of C4, C3 and C5b-9, whereas binding of C1q was hardly detectable (FIGS. 5E-H). Complement activation by mannan was only slightly inhibited by the addition of mAb 2004. Therefore, addition of mAb 2004 to serum allows the specific detection of LP activation by using mannan as ligand without any interference of the CP.

Example 6

Assessment of Functional Alternative Pathway Activity by ELISA

The protocol for the functional activity of the alternative pathway was similar to the protocol for the LP assay, Example 5, with important modifications. As a ligand for AP activation, LPS was coated at 10 µg/ml. LPS from *Salmonella typhosa* was obtained from Sigma (L-6386), dissolved in PBS at 1.6 mg/ml and stored at −20° C. Plates were blocked by using 1% BSA in PBS. Serum samples were diluted in GVB/MgEGTA (VBS containing 10 mM EGTA, 5 mM $MgCl_2$, 0.05% Tween-20, and 0.1% gelatin; pH 7.5) and incubated in the plate for 1 hour at 37° C. Complement binding was assessed by using dig-conjugated mAb directed against C4 and C3 followed by the detection of mAb binding by using HRP-conjugated sheep anti-dig antibodies.

Activation of the Alternative Pathway.

Figure 6:
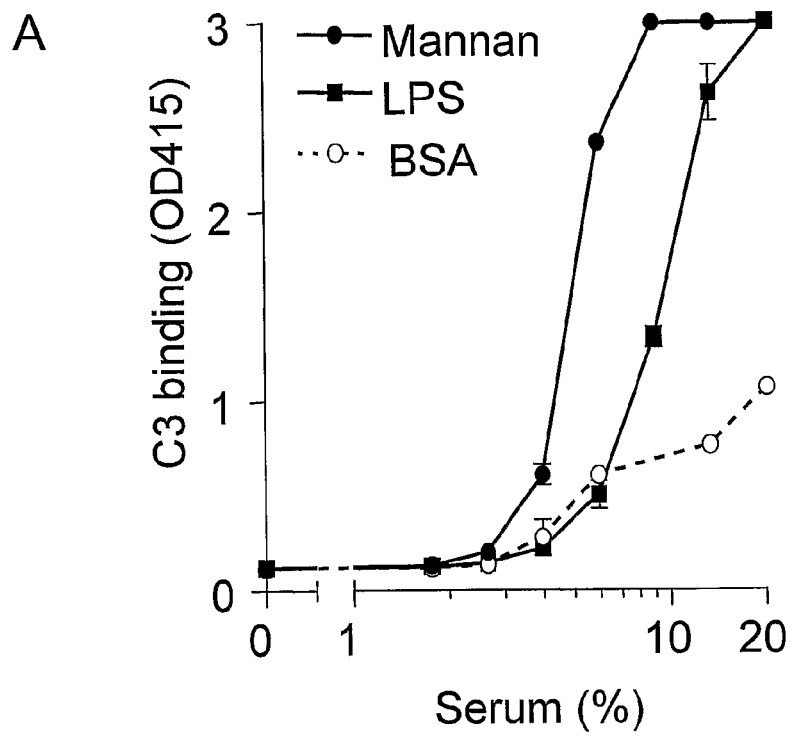
Figure 6:
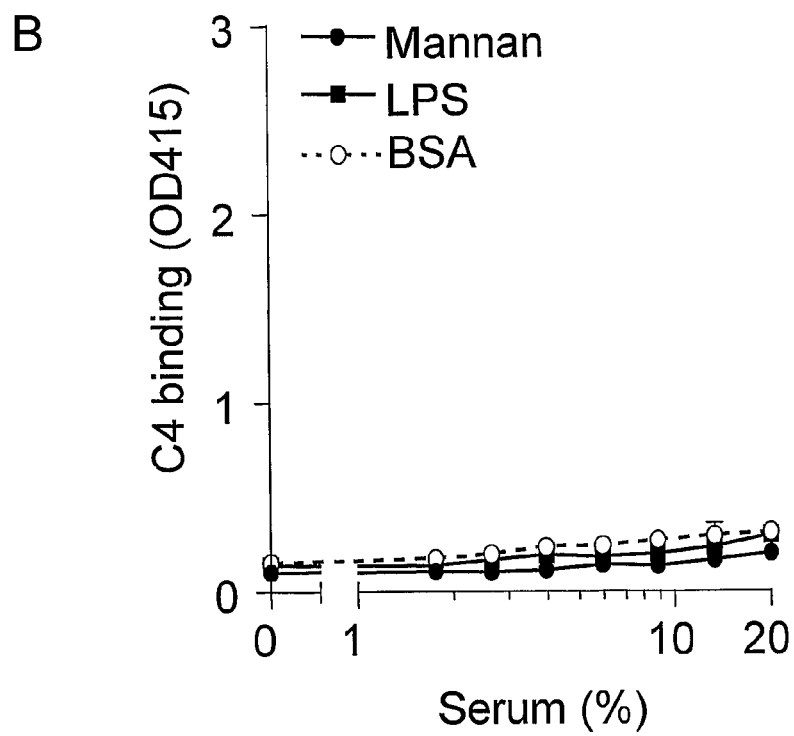

In order to enable the detection of all complement activation pathways in one assay system, the activation of the alternative pathway in an ELISA system was also studied. In contrast to the LP and the CP, activation of the AP is calcium-mdependent. Therefore, a calcium-free buffer was used, thus excluding involvement of the CP and the LP. As previously described (Fredrikson G.N., et al., *J. Immunol. Methods* 166, 263-270, 1993), incubation of NHS in a buffer containing EGTA and Mg** on plates coated with LPS resulted in a does-dependent deposition of C3 (FIG. 6). Some activation of C3 was also observed on plates coated with BSA only, most likely due to spontaneous activation of the AP. Surprisingly, a strong activation of C3 was also observed when NHS was incubated on mannan-coated plates by using the same conditions, suggesting that a mannan may also support the activation of the AP. The detection of C3 was reduced until background levels when EDTA was present in the complement source (not shown). As expected from an AP-dependent mechanism, C3 activation in calcium-free buffers required a serum concentration that is about 10-fold higher than that required for C3 activation by mannan in a calcium-containing buffer via the LP (compare FIG. 6 with FIG. 5B). Although C3 activation was clearly detectable in a calcium-free buffer (FIG. 6A), no activation of C4 could be established, suggesting that under these conditions activation of C3 (FIG. 6B) is independent of MBL binding and C4 activation.

The invention claimed is:

1. An in vitro method of functionally determining deficiencies in the Lectin Complement Pathway in a sample of blood, serum, or plasma obtained from a mammal, the method comprising the steps of
   (a) adding a C1 complex inhibitor to the sample to inhibit the Classical Complement Pathway, the C1 complex inhibitor comprising:
      an inhibitory C1q-binding proteins elected from the group consisting of C1 inhibitor, CRT, C1Qr, E. coli C1g binding protein, gC1qR, ghB3, decorin, chondroitin sulphate proteoglycan, and surfactant protein A,
      a peptide inhibitor of C1q, C1r or C1s selected from the group consisting of TDGDKAFVDFLSDEIKEE (SEQ ID NO. 1), KDIRCKDD (SEQ ID NO. 2), AEAKAKA (SEQ ID NO. 3), VQVHNAKTKPR (SEQ ID NO. 4), WY, CEGPFGPRHDLTFCW (SEQ ID NO. 5), LEQGENVFLQATLL (SEQ ID NO. 6), CRWDGSWGEVRC (SEQ ID NO. 7), CMWVRMWGDVNC (SEQ ID NO. 8), CFWAGKFGLGTC (SEQ ID NO. 9), CKDRWVVEERCC (SEQ ID NO. 10), and CWNRFKKMDRC (SEQ ID NO. 11), or
      an immunoglobulin that binds C1q, C1r or C1s;
   (b) diluting the sample with a buffered aqueous media having a pH and ion strength corresponding to the physiological pH and ion strength of the blood, serum, or plasma from the mammal in order to inhibit activation of the Alternative Complement Pathway in the sample;
   (c) adding a mannan-binding lectin (MBL) carbohydrate or ficolin binding carbohydrate to activate the Lectin Complement Pathway in the sample;
   (d) adding a first antibody to the sample that specifically binds C5b-9 complex to detect formation of C5b-9 complex in the sample, and
   (e) determining activation of the Lectin Complement Pathway in the sample at the physiological conditions by measuring the amount of C5b-9 complex detected in the sample.

2. The method according to claim 1, wherein said immunoglobulin that binds to C1q, C1r, or C1s in step (a) is an immunoglobulin selected from the group consisting of polyclonal and monoclonal antibodies.

3. The method according to claim 1, wherein said MBL carbohydrate in step (c) is an MBL carbohydrate of low molecular weight selected from the group consisting of mannose and fucose.

4. The method according to claim 1, wherein said first antibody in step (d) is a polyclonal or a monoclonal antibody.

5. The method according to claim 1, wherein the step in (d) comprises adding a second antibody that binds said first antibody, wherein said second antibody is a labeled antibody.

6. The method according to claim 1, wherein said first antibody is a labeled antibody.

7. The method according to claim 1, wherein said MBL carbohydrate in step (c) is a high molecular weight mannan.

8. The method according to claim 7, wherein said mannan is glucomannan or galactomannan.

* * * * *

SEQUENCE LISTING

```
<160> NUMBER OF SEQ ID NOS: 11

<210> SEQ ID NO 1
<211> LENGTH: 18
<212> TYPE: PRT
<213> ORGANISM: Artificial
<220> FEATURE:
<223> OTHER INFORMATION: synthetic peptide

<400> SEQUENCE: 1

Thr Asp Gly Asp Lys Ala Phe Val Asp Phe Leu Ser Asp Glu Ile Lys
1               5                   10                  15

Glu Glu
```

```
<210> SEQ ID NO 2
<211> LENGTH: 8
<212> TYPE: PRT
<213> ORGANISM: Artificial
<220> FEATURE:
<223> OTHER INFORMATION: synthetic peptide

<400> SEQUENCE: 2

Lys Asp Ile Arg Cys Lys Asp Asp
1               5

<210> SEQ ID NO 3
<211> LENGTH: 7
<212> TYPE: PRT
<213> ORGANISM: Artificial
<220> FEATURE:
<223> OTHER INFORMATION: synthetic peptide

<400> SEQUENCE: 3

Ala Glu Ala Lys Ala Lys Ala
1               5

<210> SEQ ID NO 4
<211> LENGTH: 11
<212> TYPE: PRT
<213> ORGANISM: Artificial
<220> FEATURE:
<223> OTHER INFORMATION: synthetic peptide

<400> SEQUENCE: 4

Val Gln Val His Asn Ala Lys Thr Lys Pro Arg
1               5                   10

<210> SEQ ID NO 5
<211> LENGTH: 15
<212> TYPE: PRT
<213> ORGANISM: Artificial
<220> FEATURE:
<223> OTHER INFORMATION: synthetic peptide

<400> SEQUENCE: 5

Cys Glu Gly Pro Phe Gly Pro Arg His Asp Leu Thr Phe Cys Trp
1               5                   10                  15

<210> SEQ ID NO 6
<211> LENGTH: 14
<212> TYPE: PRT
<213> ORGANISM: Artificial
<220> FEATURE:
<223> OTHER INFORMATION: synthetic peptide

<400> SEQUENCE: 6

Leu Glu Gln Gly Glu Asn Val Phe Leu Gln Ala Thr Leu Leu
1               5                   10

<210> SEQ ID NO 7
<211> LENGTH: 12
<212> TYPE: PRT
<213> ORGANISM: Artificial
<220> FEATURE:
<223> OTHER INFORMATION: synthetic peptide

<400> SEQUENCE: 7

Cys Arg Trp Asp Gly Ser Trp Gly Glu Val Arg Cys
1               5                   10

<210> SEQ ID NO 8
```

```
<211> LENGTH: 12
<212> TYPE: PRT
<213> ORGANISM: Artificial
<220> FEATURE:
<223> OTHER INFORMATION: synthetic peptide

<400> SEQUENCE: 8

Cys Met Trp Val Arg Met Trp Gly Asp Val Asn Cys
1               5                   10

<210> SEQ ID NO 9
<211> LENGTH: 12
<212> TYPE: PRT
<213> ORGANISM: Artificial
<220> FEATURE:
<223> OTHER INFORMATION: synthetic peptide

<400> SEQUENCE: 9

Cys Phe Trp Ala Gly Lys Phe Gly Leu Gly Thr Cys
1               5                   10

<210> SEQ ID NO 10
<211> LENGTH: 12
<212> TYPE: PRT
<213> ORGANISM: Artificial
<220> FEATURE:
<223> OTHER INFORMATION: synthetic peptide

<400> SEQUENCE: 10

Cys Lys Asp Arg Trp Val Val Glu Glu Arg Cys Cys
1               5                   10

<210> SEQ ID NO 11
<211> LENGTH: 11
<212> TYPE: PRT
<213> ORGANISM: Artificial
<220> FEATURE:
<223> OTHER INFORMATION: synthetic peptide

<400> SEQUENCE: 11

Cys Trp Asn Arg Phe Lys Lys Met Asp Arg Cys
1               5                   10
```